United States Patent [19]

Paul et al.

[11] Patent Number: 4,579,848

[45] Date of Patent: Apr. 1, 1986

[54] 5-SUBSTITUTED[1,2,4]TRIAZOLO[1,5-C]PYRIMIDIN-2-AMINES

[75] Inventors: Rolf Paul, River Vale; Robert A. Hardy, Jr., Ridgewood; John A. Brockman, Woodcliff Lake, all of N.J.

[73] Assignee: American Cyanamid Company, Stamford, Conn.

[21] Appl. No.: 653,403

[22] Filed: Sep. 24, 1984

Related U.S. Application Data

[63] Continuation-in-part of Ser. No. 518,250, Jul. 28, 1983, abandoned.

[51] Int. Cl.$^4$ .................. A61K 31/505; C07D 471/04
[52] U.S. Cl. ..................... 514/258; 544/263; 544/319; 544/333; 544/335
[58] Field of Search .................. 544/263; 424/251; 514/258

[56] References Cited

U.S. PATENT DOCUMENTS

| | | | |
|---|---|---|---|
| 3,045,015 | 4/1962 | Miller | 544/263 |
| 3,046,276 | 7/1962 | Miller | 544/263 |
| 3,053,844 | 9/1962 | Miller | 544/263 |
| 4,269,980 | 5/1981 | Hardy | 544/263 |
| 4,528,288 | 4/1985 | Wade | 544/263 |

FOREIGN PATENT DOCUMENTS 234982 12/1960 Australia .

Primary Examiner—Donald G. Daus
Assistant Examiner—Robert Benson
Attorney, Agent, or Firm—Edward A. Congor, Jr.

[57] ABSTRACT

This invention is concerned with 5-substituted[1,2,4]-triazolo[1,5-c]pyrimidin-2-amines selected from those of Formula I, which are active as antiasthma agents.

20 Claims, No Drawings

5-SUBSTITUTED[1,2,4]TRIAZOLO-[1,5-C]PYRIMIDIN-2-AMINES

CROSS REFERENCE TO RELATIVE PATENT APPLICATION

This application is a continuation-in-part of our co-pending application, Ser. No. 518,250 filed 7/28/83 (now abandoned).

SUMMARY OF THE INVENTION

This invention is concerned with 5-substituted [1,2,4]triazolo[1,5-c]pyrimidin-2-amines selected from those of Formula I, which are active as antiasthma agents.

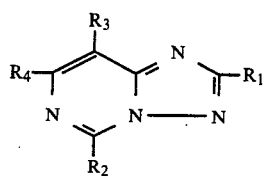

(FORMULA I)

In Formula I, $R_1$ is selected from the group consisting of amino, $(C_1-C_6)$acylamino, alkyl$(C_1-C_6)$amino and 1-chloro-2-propanolamino; $R_2$ is selected from the group consisting of mono- and disubstituted phenyl [wherein the substituents are selected from trifluoromethyl, nitro, chloro, bromo, iodo, alkyl$(C_1-C_6)$, formyl, 1-alkynyl, difluoromethoxy, carboxamido, CON[alkyl$(C_1-C_6)$]$_2$, —CON(CH$_2$)$_n$ (where n=2–5) and —COOalkyl$(C_1-C_6)$], p-methylphenylsulfonylamino, 2-, 3- and -4-pyridinyl, 3-alkyl$(C_1-C_6)$-4-pyridinyl and 4-pyridine-1-oxide; and $R_3$ and $R_4$ are individually selected from the group consisting of hydrogen and alkyl$(C_1-C_6)$.

This invention is also concerned with a series of intermediates represented by Formulae II, III and IV which are used in a sequence of reactions to produce the products of Formula I.

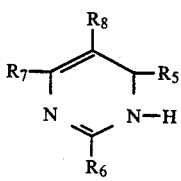

(FORMULA II)

In Formula II, $R_5$ is selected from =O and its tautomer; $R_6$ is selected from the group consisting of mono- and disubstituted phenyl [wherein the substituents are selected from trifluoromethyl, nitro, chloro, bromo, iodo, alkyl$(C_1-C_6)$, dichloromethyl, formyl, 1-alkynyl, difluoromethyoxy, carboxamido, —CON[alkyl$(C_1-C_6)$]$_2$, —CON(CH$_2$)$_n$ (where n=2–5) and —COOalkyl$(C_1-C_6)$], and 3-pyridinyl; and $R_7$ and $R_8$ are selected from the group consisting of hydrogen and alkyl$(C_1-C_6)$.

With regard to Formula II, the compound where $R_6$ would be 2-pyridinyl is disclosed in O. Kirino, et al., Agric. Biol. Chem., 41, 1093 (1977).

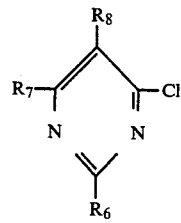

FORMULA III

In Formula III, $R_6$, $R_7$ and $R_8$ are the same as described in Formula II and the compound $R_6$=4-pyridinyl and $R_7$=hydrogen is disclosed in G. Y. Lesher, et al., J. Med. Chem., 25, 837 (1982).

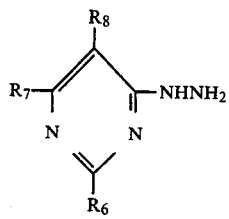

FORMULA IV

In Formula IV, $R_6$ is selected from the group consisting of mono- and disubstituted phenyl [wherein the substituents are selected from nitro, alkyl$(C_1-C_6)$, dichloromethyl, formyl, difluoromethoxy, carboxamido, —CON[alkyl$(C_1-C_6)$]$_2$, —CON(CH$_2$)$_n$ (where n=2–5) and —COOalkyl$(C_1-C_6)$], and $R_7$ and $R_8$ are selected from the group consisting of hydrogen and alkyl$(C_1-C_6)$.

With regard to Formula IV, compounds where $R_6$ is phenyl substituted by trifluoromethyl, halogen or alkoxy and $R_7$ and $R_8$ are hydrogen are disclosed in U.S. Pat. No. 4,269,980.

In addition, this invention is concerned with a method of treating asthma and allergic diseases in warm-blooded animals and with compositions of matter employing the compounds of Formula I.

Further, this invention is concerned with a process of producing the compounds of Formula I.

DESCRIPTION OF THE INVENTION

The products of the present invention may be prepared according to the following flowcharts.

FLOWCHART I

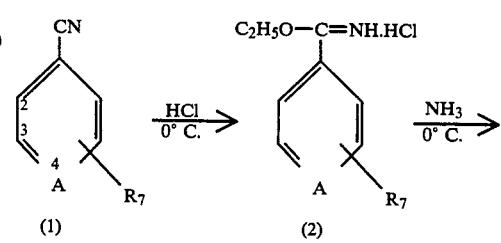

FLOWCHART I

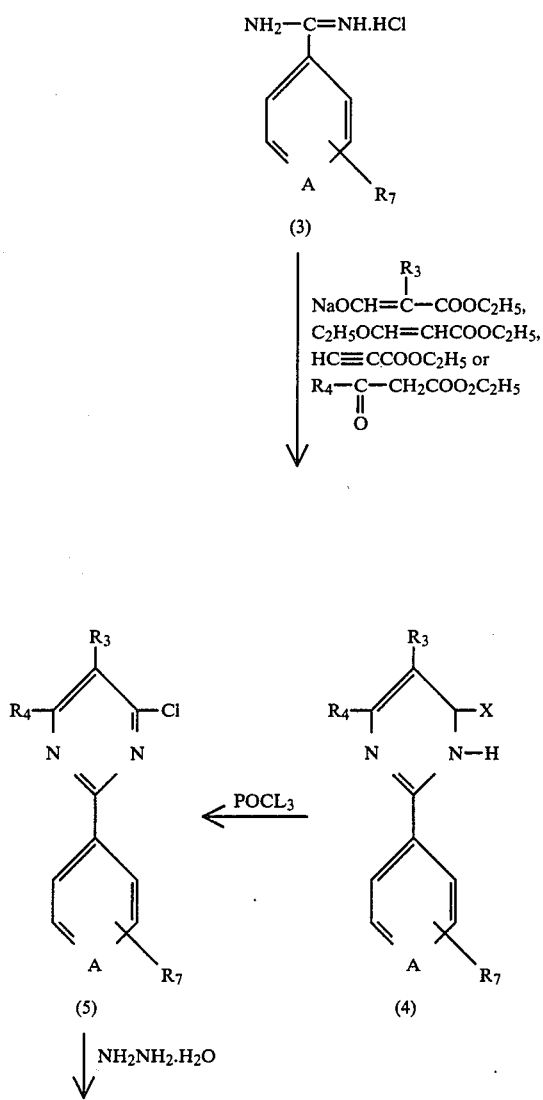

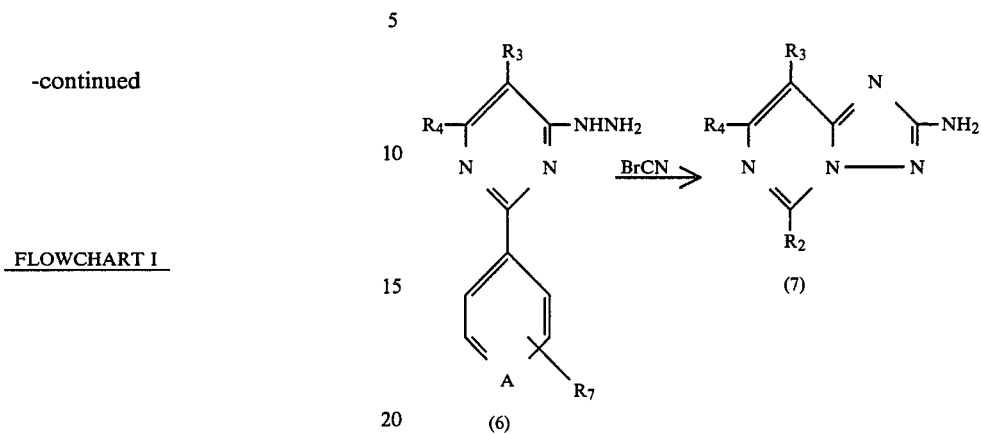

In accordance with the above flowchart, a substituted nitrile (A is —CH$_2$—) or pyridinylnitrile (where A is —N= and may be at position 2,3 or 4) where R$_7$ is trifluoromethyl, nitro, chloro, bromo, iodo, alkyl(-C$_1$-C$_6$), —CON[alkyl(C$_1$-C$_6$)]$_2$, —CON(CH$_2$)$_n$ (where n=2-5), —COOalkyl(C$_1$-C$_6$), formyl or difluoromethyoxy (1) in a solvent mixture of methanol and ether at 0° C. is saturated with hydrogen chloride gas and stored at 0° C. for 12–48 hours giving (2) which is then dissolved in absolute ethanol at 0° C., saturated with ammonia gas and stored at 0° C. for 48–288 hours giving (3). The compounds (3) are then neutralized with an alkali in chloroform providing the free base which after concentration in vacuo is then dissolved in absolute ethanol and reacted with either ethyl 3-ethoxy-2-propenoate, ethyl formylpropionate, sodium salt ethyl formylpropiolate, ethyl formylacetate sodium salt, or ethyl alkanoyl acetate at reflux for several days, giving (4), where R$_3$ and R$_4$ are lower alkyl(C$_1$-C$_6$), X is =O or its tautomer, and A and R$_7$ are as described above. The pyrimidinols or pyrimidinones (4) are then reacted with phosphorous oxychloride with warming for 1–24 hours poured over ice, collected and recrystallized giving (5). The compounds (5) are dissolved in methanol and reacted with hydrazine hydrate with heating for 1–4 hours, then cooled, giving the hydrazine interemediates (6). The hydrazines (6) are dissolved in methanol and reacted with cyanogen bromide at reflux for several hours giving the products (7) where R$_2$, R$_3$ and R$_4$ are as described above for Formula I.

FLOWCHART II

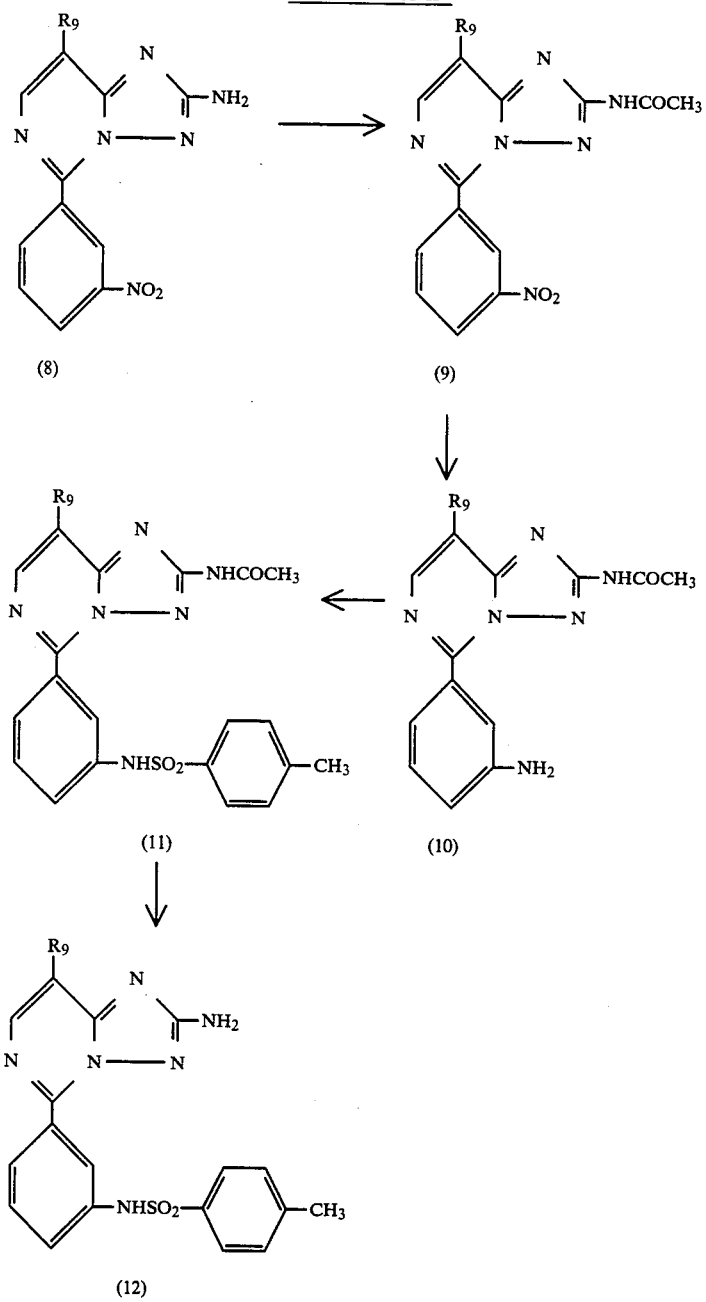

In accordance with Flowchart II, the nitro compound (8) is acetylated with acetic anhydride to give (9) which is then reduced with hydrogen using a catalyst such as palladium, giving the amino amide (10) Reaction of (10) with p-toluenesulfonyl chloride in pyridine gives (11) which is then hydrolyzed using 1N hydrochloric acid in dioxane, giving (12), where $R_9$ is hydrogen or lower alkyl($C_1$–$C_6$).

FLOWCHART III
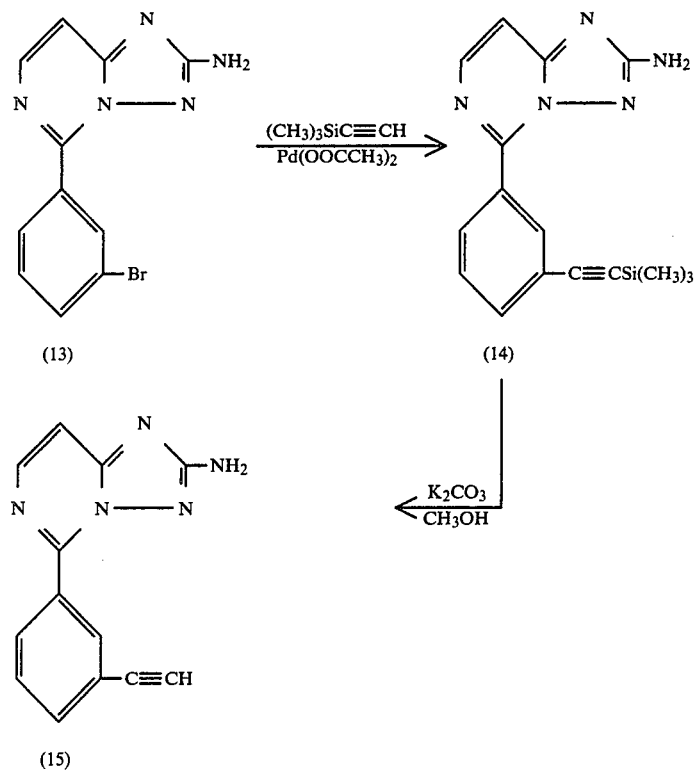
As shown in Flowchart III, 5-(3-bromophenyl)[1,2,4]triazolo[1,5-c]pyrimidin-2-amine (13) is converted to (14) using ethynyl trimethylsilane, palladium II acetate and triethylphosphine followed by deprotection using potassium carbonate.
FLOWCHART IV
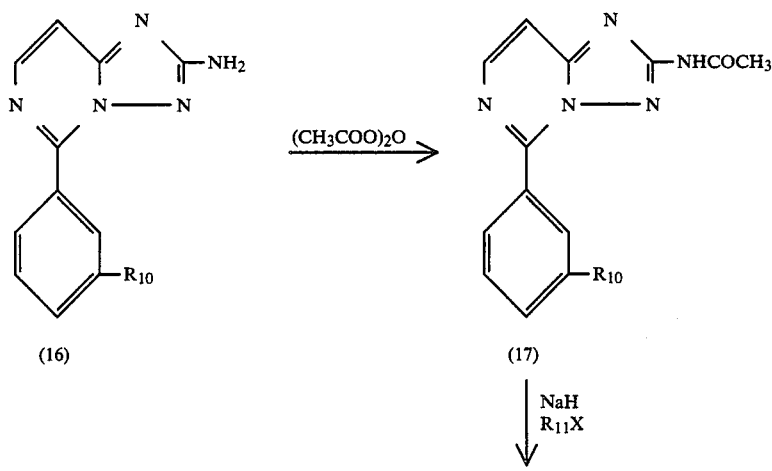

FLOWCHART IV

-continued

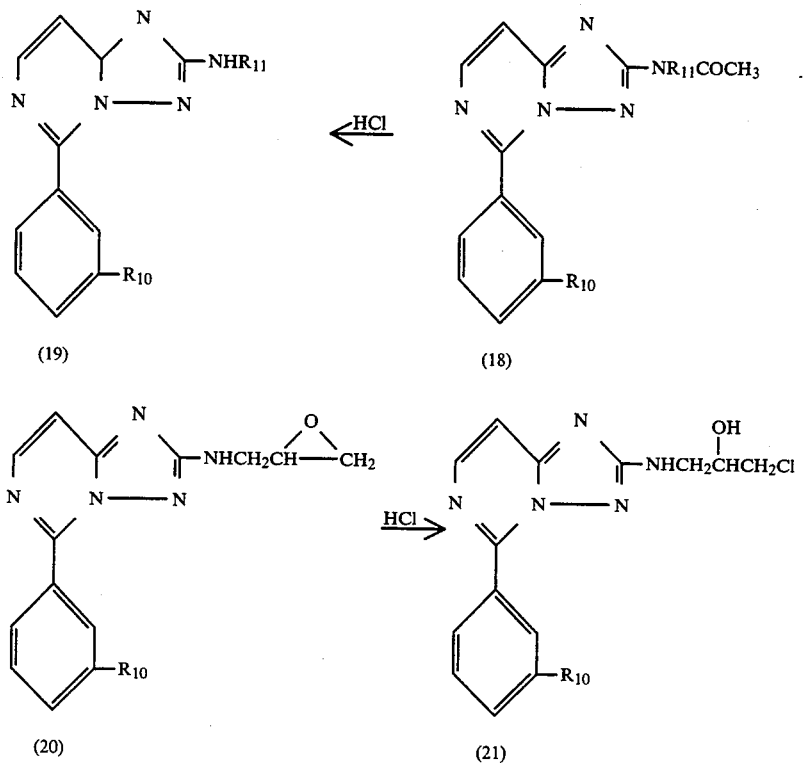

In Flowchart IV compound (16), where $R_{10}$ is selected from trifluoromethyl, nitro, chloro, bromo, iodo or alkyl($C_1$–$C_6$), is acetylated to give (17) which is then treated with sodium hydride followed by an alkylating agent $R_{11}X$, where $R_{11}$ is alkyl and X is halide, or epichlorohydrin, giving (18). Mild hydrolysis with dilute acid at room temperature removes the acetyl group and gives (19), a 2-substituted amino[1,2,4]triazolo[1,5-c]pyrimidine. In the case where $R_{11}$ is a 2,3-epoxypropyl group (20), 6N hydrochloric acid opens the epoxy ring to give (21).

FLOWCHART V

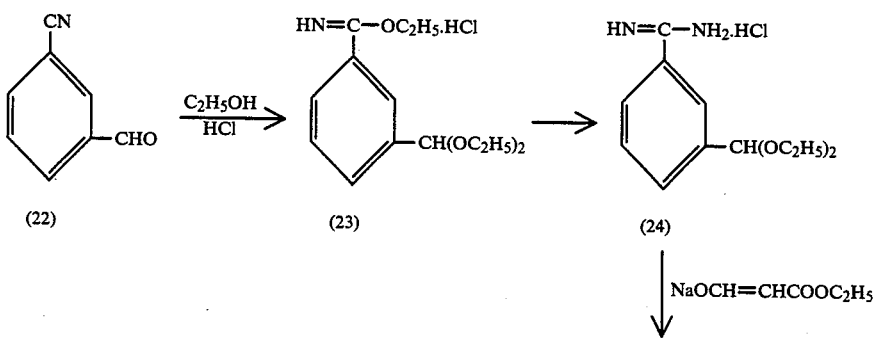

-continued
FLOWCHART V

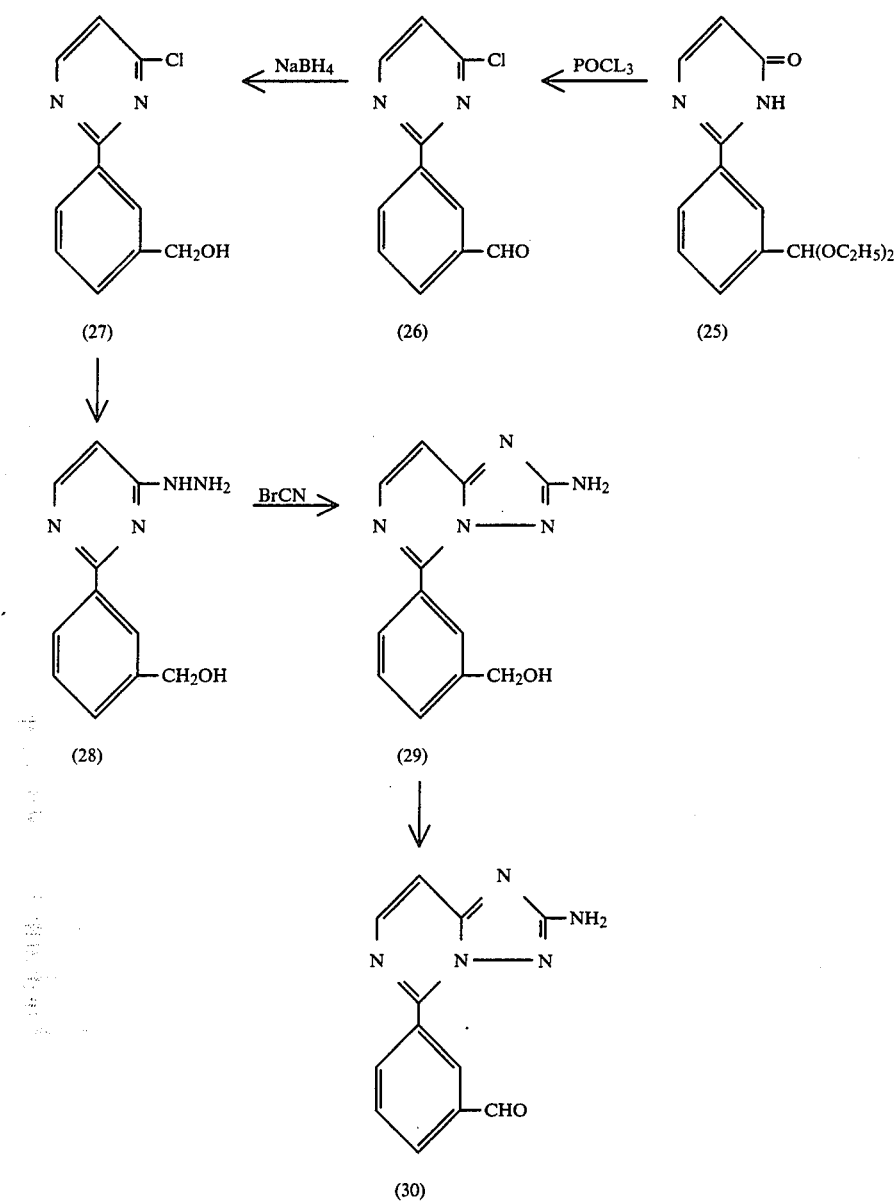

Flowchart V shows the preparation of 3-(2-amino[1,2,4]triazolo[1,5-c]pyrimidin-5-yl)benzaldehyde. During the conversion of 3-cyanobenzaldehyde (22) to the iminoether (23) an acetal is also formed. Conversion to the amidine (24) and pyrimidine (25) is accomplished by the procedures outlined hereinabove. On preparing the chloropyrimidine (26), the aldehyde functionality is reformed. Reduction produces the alcohol (27) which is converted to (29) by the general procedure of Flowchart I. Reoxidation of (29) using diethylaminopyridinium chlorochromate gives (30).

The novel compounds of the present invention are highly active as antiasthmatic and antiallergic agents as will be demonstrated hereinbelow.

The bronchospasm of allergic asthma is a consequence of the release of mediators, such as histamine and slow-reacting substances from mast cells. The role of mediator release in the induction of an asthmatic attack has been fully reviewed and documented, see Kaliner, M. and Austen, K. F., Bronchial Asthma Mechanisms and Therepautics, E. B. Weiss, Editor, Little, Brown and Company, Boston, 1976, p. 163; Lichtenstein, L. M., Asthma-Physiology, Immunopharmacology and Treatment, Second International Symposium, L. M. Lichtenstein and K. F. Austen, Editors, Academic Press, New York, 1979, p. 51; and Bell, S. C., et al., Annular Reports in Medicinal Chemistry, 14, H. J. Hess, Editor, Academic Press, New York, 1979, p. 51.

The novel compounds of this invention have been tested by the procedure of Lichtenstein, L. M. and Osler, A. G., J. Exp. Med., 120, 507–530 (1964), which evaluates the ability of compounds to inhibit mediator (histamine) release from immunologically stimulated human basophils.

Reagents

10X Concentrated Tris Buffer

Dissolve 140.3 g of sodium chloride, 7.45 g of potassium chloride and 74.5 g of Trizma-Tris Pre-Set, Reagent Grade, pH 7.6, at 25° C. (Sigma Chemical Co.) in sufficient water to give a final volume of 2 liters.

Human Albumin (Sigma Chemical Co.) (30 mg/ml)

Calcium and Magnesium Stocks

Made to 0.075M and 0.5M respectively, with calcium chloride dihydrate and magnesium chloride hexahydrate.

Tris-A Buffer

A 10 ml portion of 10X Tris Buffer and 1.0 ml of human albumin are diluted to 100 ml with water.

Tris ACM Buffer

A 10 ml portion of 10X Tris Buffer, 1.0 ml of human albumin, 0.8 ml of calcium stock and 0.2 ml of magnesium stock are diluted to 100 ml with water.

Rabbit Antihuman IgE

Behring Diagnostics (Generally used at 10 μg protein/ml final concentration.)

House Dust Mite Extract (*Dermatophagoides Farinae*)

Strength 1:100 (w:v) allergenic extract, Hollister-Stier Labs. Generally this is diluted 1:1000 to 1:10,000 (considering the vial as stock).

Other Allergens

Intradermal solutions or intramuscular preparations for hyposensitization, Hollister-Stier Labs. The final concentration used is on the order of 1 PNU/ml.

Separation of Leukocytes from Human Blood and Challenge

Eighty milliliters of blood is withdrawn from subjects with known histamine release to anti-IgE, ragweed antigen or other specific allergen, using four 20 ml heparinized tubes. This 80 ml of blood is mixed with 20 ml of saline containing 0.6 g of dextrose and 1.2 g of dextran. The blood is allowed to sediment at room temperature in two 50 ml polycarbonate centrifuge tubes until a sharp interface develops between the red cells and plasma (60–90 minutes). The plasma (top) layer from each tube is withdrawn by pipet and transferred to respective 50 ml polycarbonate tubes. The plasma is centrifuged for 8 minutes at 110X g at 4° C. The supernatant is carefully poured off as completely as possible and the cell button is resuspended in 2-3 ml of Tris-A buffer using a siliconized Pasteur pipet. The resuspension is accomplished by drawing the liquid gently in and out of the pipet, with the tip below the liquid, until an even suspension of cells is obtained. Sufficient Tris-A buffer is then added to bring the volume in the tube to about 45 ml and the tube is centrifuged at 110X g for 8 minutes at 4° C. The supernatant is poured off and the cell button is resuspended and centrifuged as described above. The supernatant is poured off and the cell button is suspended in 2-3 ml of Tris-ACM buffer to make the final volume sufficient to allow addition to the reaction tubes.

Reaction tubes containing anti-IgE or antigens, either alone or with test compound in a total volume of 0.2 ml are prepared and placed in a 37° C. bath. The cells are warmed to 37° C. and frequently swirled to ensure an even suspension, while 1.0 ml aliquots are added to each reaction tube. The tubes are then incubated for 60 minutes at 37° C., vortexing the tubes gently every 15 minutes to keep the cells evenly suspended. When the reaction is complete, the tubes are centrifuged at 4° C. for 10 minutes at 1500 rpm to sediment the cells. One ml aliquots of supernatant are transferred to 12X 75 mm polyethylene tubes and 0.2 ml of 8% perchloric acid is added to each tube. Blanks and totals are included in each test. The blanks have cells and all reagents except antigen or anti-IgE. The totals contain 0.24 ml of 8% perchloric acid, one ml of cells and 0.2 ml of buffer. All samples are then centrifuged to remove the precipitate protein.

Assay of Released Histamine by the Automated Fluorometric Method

This automated method has been described by Siraganian, R. P., in Anal. Biochem., 57, 383 (1974) and J. Immunol. Methods, 7, 283 (1975) and is based on the manual method of Shore, P. A., et al., J. Pharmacol. Exp. Ther., 217, 182 (1959).

The automated system consists of the following Technicon Autoanalyzer II components: Sampler IV, Dual-Speed Proportioning Pump III, Fluoronephelometer with a narrow pass primary filter 7–60 and a secondary filter 3–74, Recorder, and Digital Printer. The manifold used is the one described by Siraganian vide supra, with the following modifications: the dialyzer is omitted; all pumping tubes pass through a single proportioning pump with large capacity and twice the volume of sample is taken for analysis.

The automated chemistry consists of the following steps: Extraction from alkaline saline into butanol, back extraction into dilute hydrochloric acid by addition of heptane, reaction of histamine with o-phthaldialdehyde (OPT) at high pH and conversion of the OPT adduct to a stable fluorophore with phosphoric acid. The reaction product is then passed through the fluorometer. The full scale response is adjusted to 50 ng histamine base with a threshold sensitivity of approximately 0.5 ng.

Calculation of the Results of Histamine Release Tests

The instrument blank (wash) is subtracted from the ng histamine of each sample. Then the ng histamine of each sample is divided by the mean of the three totals (cells lysed with perchloric acid) to obtain percent release.

Control samples contain antigen but no test compound. Blank (or spontaneous release) samples contain neither antigen nor test compound. The mean of the blanks (three replicates) is subtracted from the percent release for controls and test compounds.

The means for control and test compound groups are computed and the result for a test compound is computed as percent of control by the formula:

$$100 \times \frac{\% \text{ Histamine Release with Test Compound}}{\% \text{ Histamine Release in Controls}}$$

Values obtained at different concentrations of test compound are used to calculate an $ED_{50}$ (the concentration in μM which causes a 50% inhibition of histamine release) by linear regression.

The results of this test on typical compounds of this invention appear in Table I.

TABLE I

Inhibition of Histamine Release From Immunologically Stimulated Human Basophils

| Compound | $ED_{50}$ μM |
|---|---|
| 5-(3-Methylphenyl)[1,2,4]triazolo[1,5-c]-pyrimidin-2-amine | 7.8 |
| 8-Methyl-5-(3-nitrophenyl)[1,2,4]triazolo-[1,5-c]pyrimidin-2-amine | 8.7 |
| 5-[3,5 -Bis(trifluoromethyl)phenyl][1,2,4]tria- | 0.7 |

TABLE I-continued

Inhibition of Histamine Release From Immunologically Stimulated Human Basophils

| Compound | ED$_{50}$ μM |
|---|---|
| zolo[1,5-c]pyrimidin-2-amine | |
| 3-(2-Amino[1,2,4]triazolo[1,5-c]pyrimidin-5-yl)-N,N—dimethylbenzamide | 11 |
| 3-(2-Amino[1,2,4]triazolo[1,5-c]pyrimidin-5-yl)-benzoic acid, ethyl ester | 11 |
| 4-(2-Amino[1,2,4]triazolo[1,5-c]pyrimidin-5-yl)-benzoic acid, ethyl ester | 16 |
| 5-[3-(Dichloromethyl)phenyl][1,2,4]triazolo-[1,5-c]pyrimidin-2-amine | 1.2 |
| 5-(3-Bromophenyl)[1,2,4]triazolo[1,5-c]pyrimidin-2-amine | 3.3 |
| 5-[3-(Difluoromethoxy)phenyl][1,2,4]triazolo-[1,5-c]pyrimidin-2-amine | 3 |
| 5-(3-Methyl-4-pyridinyl)[1,2,4]triazolo[1,5-c]pyrimidin-2-amine | 3.8 |
| 5-[3-(Trifluoromethyl)phenyl][1,2,4]triazolo-[1,5-c]pyrimidin-2-amine | 2.7 |
| 5-(4-Fluorophenyl)[1,2,4]triazolo[1,5-c]pyrimidin-2-amine | 31 |
| 5-(3-Chlorophenyl)[1,2,4]triazolo[1,5-c]pyrimidin-2-amine | 4.3 |
| 5-(3-Nitrophenyl)[1,2,4]triazolo[1,5-c]pyrimidin-2-amine | 3.8 |
| 8-Methyl-5-[3-(trifluoromethyl)phenyl][1,2,4]-triazolo[1,5-c]pyrimidin-2-amine | 5.6 |
| 5-(3-Pyridinyl)[1,2,4]triazolo[1,5-c]pyrimidin-2-amine | 49.4 |
| 5-(4-Pyridinyl)[1,2,4]triazolo[1,5-c]pyrimidin-2-amine | 33 |
| 5-[3-(Trifluoromethyl)phenyl][1,2,4]triazolo-2-acetamide | 20 |
| N—[8-Methyl-5-(3-nitrophenyl)[1,2,4]triazolo-[1,5-c]pyrrimidin-2-yl]acetamide | 11 |
| N—[8-Methyl-5-[3-[[(4-methylphenyl)sulfonyl]-amino]phenyl][1,2,4]triazolo[1,5-c]pyrimidin-2-yl]acetamide | 34.4 |
| N—Methyl-5-[3-(trifluoromethyl)phenyl][1,2,4]-triazolo[1,5-c]pyrimidin-2-amine | 16 |
| 3-(2-Amino[1,2,4]triazolo[1,5-c]pyrimidin-5-yl)benzaldehyde | 0.8 |
| 5-(4-Pyridinyl)[1,2,4]triazolo[1,5-c]pyrimidin-2-amine, pyridine-1-oxide | 4.9 |
| 1-Chloro-3-[[5-[3-(trifluoromethyl)phenyl]-[1,2,4]triazolo[1,5-c]pyrimidin-2-yl]amino]-2-propanol | 9.5 |
| N—5-[3-[[(4-Methylphenyl)sulfonyl]amino]-phenyl]-[1,2,4]triazolo[1,5-c]pyrimidin-2-yl]acetamide | 1.7 |
| N—[3-(2-Amino[1,2,4]triazolo[1,5-c]pyrimidin-5-yl)phenyl]-4-methylbenzenesulfonamide | 1.5 |
| 5-(3-Ethynylphenyl)[1,2,4]triazolo[1,5-c]pyrimidin-2-amine | 14 |
| 7-Methyl-5-[3-(trifluoromethyl)phenyl][1,2,4]-triazolo[1,5-c]pyrimidin-2-amine | 100 |

Passive Anaphylaxis Test

At —48 hours (relative to antigen challenge at time 0), 2 ml of saline containing 0.2–0.05 IgG hyperimmune serum (depending on batch of antibody used) was injected intraperitoneally (i.p.) into 250–300 g female Hartley-strain guinea pigs. One hour before challenge, the test compound is given to ten animals orally at 4 ml/kg of a suspension in 0.5% carboxymethylcellulose. The standard dose is 50 mg/kg. Ten control animals receive the vehicle only. The challenge consists of an intravenous injection of 0.25–2.0 mg of ovalbumin in one ml of saline. The time to the first observable symptom of anaphylaxis (normally this is a scratching of the nose) and the time to loss of righting reflex are recorded for each animal. Thirty minutes after the challenge the numbers of deceased and living animals are also recorded.

The treated and control groups are compared by a Mann-Whitney rank sum test for the times to symptom and times to collapse. In addition, a Fisher's exact test is done on the number of collapsed vs. noncollapsed for control and treated groups. If the Fisher test is significant, the compound is considered active. If the rank sum test is significant, the compound is considered to have weak activity.

Results of the hereinabove described test with 5-(2-pyridinyl[1,2,4]triazolo[1,5-c]pyrimidin-2-amine showed it to be active.

The novel compounds of the present invention are effective as antiasthmatic agents in mammals when administered in amounts ranging from about 0.1 mg to about 100 mg/kg of body weight per day. A preferred dosage regimen for optimum results would be from about 0.1 mg to about 25 mg/kg of body weight per day, and such dosage units are employed that a total of from about 7 mg to about 1.8 g of the active compound for a subject of about 70 kg of body weight are administered in a 24 hour period. This dosage regimen may be adjusted to provide them optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, aerosol, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers suppositories and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol and polyethylene glycols. The polyethylene glycols consist of a mixture of non-volatile, normally liquid, polyethylene glycols which are soluble in both water and organic liquids and which have molecular weights of from about 200 to 1500. Although various mixtures of the aforementioned non-volatile polyethylene glycols may be employed, it is preferred to use a mixture having an average molecular weight of from about 200 to about 400.

In addition to the active compound, the parenteral solutions may contain various preservatives which may be used to prevent bacterial and fungal contamination. Such preservatives are, for example, myristyl-gamma picolinium chloride, phenyl mercuric nitrate, benzalkonium chloride, phenethyl alcohol, p-chlorophenyl-α-glycerol ether, methyl and propyl parabens and thimerosal. As a practical matter, it is also convenient to employ antioxidants. Suitable antioxidants include, for example, sodium bisulfite, sodium metabisulfite and sodium formaldehyde sulfoxylate. Generally, from about 0.05 to about 0.2% concentrations of antioxidant are employed. These compounds may also be administered by inhalation using conventional Aerosol ® formulations.

The invention will be described in greater detail in conjunction with the following specific examples.

EXAMPLE 1

3-Cyano-N,N-dimethylbenzamide

A mixture of 85.22 g of m-cyanobenzoic acid, 400 ml of toluene, 4.48 ml (4.23 g) of N,N-dimethylformamide and 44.4 ml (72.3 g) of thionyl chloride was gently heated on a steam bath for 2 hours with sulfur dioxide and hydrogen chloride being evolved. The reaction solution was cooled in an ice bath and cautiously added portionwise, over one hour, to stirred and cooled solution of 250 ml of 40% aqueous diethylamine and 100 ml of water. At intervals 2–3 ml of concentrated aqueous potassium hydroxide was added. After the addition was complete, the mixture was stirred for several hours, then the layers were separated and the organic layer washed with water. After permitting the organic layer to evaporate to dryness, the residue was recrystallized from 300 ml of ethanol containing charcoal, giving 68.5 g of the desired compound as white crystals, mp 85°–88° C.

EXAMPLE 2

3-(Difluoromethoxy)benzaldehyde

A solution was made of 200 g of 3-hydroxybenzaldehyde in 1350 ml of 2-propanol and 510 ml of water. Chlorodifluoromethane was bubbled into the solution for 5 minutes at which time a solution of 72.1 g of sodium hydroxide in 172 ml of water was added over 5 minutes. After bubbling the gas for 2 hours more, the reaction was allowed to stand for 2 days. The reaction mixture was filtered and the precipitate washed with 250 ml of 2-propanol. The combined filtrate and wash was concentrated in vacuo to 700 ml and was treated with 800 ml of 1N sodium hydroxide. The product was extracted into ether, backwashed with water, dried over sodium sulfate and concentrated in vacuo to a reddish oil. Distillation of this oil gave 61 g of the desired compound as a clear liquid, bp 65°–70° C./0.4 mm.

EXAMPLE 3

3-(Difluoromethoxy)benzaldehyde Oxime

A 2.0 g portion of hydroxylamine hydrochloride was dissolved in 12 ml of water and 8 ml of 5N sodium hydroxide was added. A 1.0 g portion of 3-(difluoromethoxy)benzaldehyde was added followed by enough ethanol to give a solution. After 10 minutes of reflux, the reaction mixture was concentrated in vacuo and the residue taken up in 10 ml of water. The pH was adjusted to 4 with hydrochloric acid, then the mixture was extracted with chloroform. The organic phase was dried over sodium sulfate and concentrated, giving the desired compound as an oil.

EXAMPLE 4

3-(Difluoromethoxy)benzonitrile

A solution of 4.95 g of 3-(difluoromethoxy)benzaldehyde oxime in 50 ml of dry tetrahydrofuran was treated with 4.30 g of N,N-carbonyldiimidazole. After the effervescence had subsided, the reaction solution was allowed to stand overnight, then concentrated in vacuo. The residue was taken up in 75 ml of water and the pH adjusted to 4 with hydrochloric acid. The nitrile was extracted into ether, dried over sodium sulfate and concentrated, giving a yellow oil which upon distillation gave 2.45 g of the desired compound as a colorless oil, bp 73°–75° C./0.3 mm.

EXAMPLE 5

3-(N,N-Dimethylamido)benzimidamide, hydrochloride

Amidines were made by the Pinner Reaction [A. Pinner and F. Klein, Ber., 10, 1889 (1877)] and were generally used crude in further reactions.

A solution of 80.8 g of N,N-dimethyl-3-cyanobenzamide in 700 ml of ethanol was saturated with hydrogen chloride gas at 0° C. After standing at 0° C. overnight, the clear solution was concentrated under aspirator vacuum at 50°–60° C. The residual oil was dissolved in 500 ml of ethanol and saturated with ammonia at 0° C. After standing at 0° C. overnight, the mixture was filtered and the filtrate concentrated in vacuo. The residual amidine was used in future reactions without further purification.

Using the general procedure of Example 5 and the indicated starting materials the compounds of Examples 6–8, found in Table II were prepared.

TABLE II

| Example | Starting Material | Compound | MP °C. |
|---|---|---|---|
| 6 | 3,5-ditrifluoromethylbenzonitrile | 3,5-ditrifluoromethylbenzamidine, hydrochloride | 124–128 |
| 7 | 3-cyanobenzaldehyde | 3-diethoxymethylbenzamidine, hydrochloride | |
| 8 | 3-difluoromethoxybenzonitrile | 3-difluoromethoxybenzamidine, hydrochloride | |

EXAMPLE 9 and the indicated reactants, the intermediates of Examples 11-23, found in Table III were obtained.

TABLE III

| Example | Starting Material | Reactant | Intermediate | MP °C. |
|---|---|---|---|---|
| 11 | 3-nitrobenzamide | ethyl formylpropionate, sodium salt | 5-methyl-2-(3-nitrophenyl)-4(3-H)—pyrimidinol | 320-232 |
| 12 | Example 6 | ethyl formylpropionate, sodium salt | 2-(3,5-ditrifluoromethylphenyl)-4(3H)—pyrimidinone | 231-232 |
| 13 | Example 5 | ethyl propiolate | 2-(N,N—dimethylamidophenyl)-4(3H)—pyrimidinone | 163-165 |
| 15 | p-ethoxycarbonylbenzamidine | ethyl propiolate | 2-(4-ethoxycarbonylphenyl)-4(3H)—pyrimidinone | 270-320 (dec.) |
| 16 | Example 7 | ethyl formylacetate, sodium salt | 2-(3-diethoxymethylphenyl)-4(3H)—pyrimidinone | 126-128 |
| 17 | 3-bromobenzamidine, hydrochloride | ethyl propiolate | 2-(3-bromophenyl)-4(3H)—pyrimidinone | 207-208 |
| 18 | Example 8 | ethyl formylacetate, sodium salt | 2-(3-difluoromethoxyphenyl)-4(3H)—pyrimidinol | 187-189 |
| 19 | Example 9 | ethyl formylacetate, sodium salt | 2-(3-methyl-4-pyridinyl)-4(1H)—pyrimidinone | 186-189 |
| 20 | m-nitrobenzamidine, hydrochloride | ethyl formylacetate, sodium salt | 2-(3-nitrophenyl)-4(3H)—pyrimidinone | |
| 21 | 3-pyridinylbenzamidine | ethyl formylpropionate, sodium salt | 2-(3-pyridinyl)-4-pyrimidinol | 188-191 |
| 22 | 3-trifluoromethylbenzamidine, hydrochloride | ethyl formylpropionate, sodium salt | 5-methyl-2-[3-(trifluoromethyl)phenyl]-4(1H)—pyrimidinone | 210-212 |
| 23 | 3-trifluoromethylbenzamidine, hydrochloride | ethyl acetoacetate | 6-methyl-2-[3-(trifluoromethyl)phenyl]-4(3H)—pyrimidinone | 211-217 |

2-Methyl-4-pyridinecarboximidamide, hydrochloride

A 17.2 g portion of 4-cyano-2-picoline [E. Ochiai and I. Suzuki, Pharm. Bull. (Japan), 2, 147 (1954)] was dissolved in 150 ml of methanol, 756 mg of sodium methoxide was added and the mixture was stirred overnight. A 7.9 g portion of ammonium chloride was added and the mixture was heated to reflux, then cooled to room temperature, giving 15 g of the desired compound, mp 168°-178° C.

EXAMPLE 10

2-(3-Tolyl)-4-pyrimidinol

A 92.3 g portion of 3-methylbenzamidine, hydrochloride [J. B. Ekeley, et al., J. Am. Chem. Soc., 57, 381 (1935)] was stirred with 200 ml of 5N sodium hydroxide and 400 ml of chloroform for ½ hour. When solution was complete the chloroform layer was separated and the aqueous layer extracted twice with 50 ml portions of chloroform. The chloroform solutions were combined, dried over sodium sulfate and evaporated, giving 69.3 g of free benzamidine. This benzamidine was taken up in one liter of absolute ethanol, 71.6 g of ethyl formylacetate sodium salt was added and the mixture was refluxed for 3 days. After cooling, the ethanol was evaporated and the residue dissolved in one liter of water and filtered. The pH of the filtrate was adjusted to 6 with 1N hydrochloric acid and the solid was collected and dried, giving 59.1 g of the desired intermediate as a white solid, mp 148°-149.5° C.

Following the general procedure of Example 10 and using the indicated starting materials, some of which are literature compounds and/or commercial compounds,

EXAMPLE 24

4-Chloro-2-(3-tolyl)-pyrimidine

A 23.91 g portion of 2-(3-tolyl)-4-pyrimidinol was mixed with 400 ml of phosphorous oxychloride in a one liter round bottom flask, under a drying tube and heated on a steam bath overnight. The mixture was allowed to cool and then poured over 2 liters of ice. The resulting solid was collected, washed with 50 ml of ether, dried and recrystallized from 100 ml of ethanol, giving 16.23 g of the desired intermediate, mp 74°-75° C.

Following the procedure of Example 24 and using the indicated precursors, the intermediates of Examples 25-37, found in Table IV, were obtained.

TABLE IV

| Example | Precursor | Intermediate II | MP °C. |
|---|---|---|---|
| 25 | Example 11 | 4-chloro-5-methyl-2-(3-nitrophenyl)-pyrimidine | 160-162 |
| 26 | Example 12 | 4-chloro-2-(3,5-ditrifluoromethylphenyl)-pyrimidine | 24-26 |
| 27 | Example 13 | 4-chloro-2-(N,N—dimethylamidophenyl)-pyrimidine | oil |
| 28 | Example 14 | 4-chloro-2-(3-ethoxycarbonylphenyl)-pyrimidine | 87-89 |
| 29 | Example 15 | 4-chloro-2-(4-ethoxycarbonylphenyl)-pyrimidine | 94-96.5 |
| 30 | Example 17 | 4-chloro-2-(3-bromophenyl)-pyrimidine | 125-126.5 |
| 31 | Example 18 | 4-chloro-2-(3-difluoromethoxyphenyl)-pyrimidine | 54-55 |
| 32 | Example 19 | 4-chloro-2-(3-methyl-4-pyridinyl)-pyrimidine | 89-90 |
| 33 | Example 22 | 4-chloro-5-methyl-2-[3-trifluoromethyl)phenyl]-pyrimidine | 98-100.5 |

TABLE IV-continued

| Example | Precursor | Intermediate II | MP °C. |
|---|---|---|---|
| 34 | Example 20 | 4-chloro-2-(3-nitrophenyl)-pyrimidine | 156–158 |
| 35 | 2-(2-pyridinyl)-4-pyrimidinol | 4-chloro-2-(2-pyridinyl)-pyrimidine | 87–89 |
| 36 | Example 21 | 4-chloro-2-(3-pyridinyl)-pyrimidine | 87–89 |
| 37 | Example 23 | 4-chloro-6-methyl-2-[3-(trifluoromethyl)phenyl]-pyrimidine | 59–61 |

EXAMPLE 38

3-(4-Chloro-2-pyriminyl)benzaldehyde and 4-Chloro-2-(3-dichloromethylphenyl)-pyrimidine A 5.3 g portion of 2-(3-diethoxymethylphenyl)-4(3H)-pyrimidinone and 30 ml of phosphorous oxychloride was heated on a steam bath overnight. The excess phosphorous oxychloride was removed under vacuum and the residue taken up in chloroform and passed through a hydrous magnesium silicate pad. Evaporation of the filtrate left 3.1 g of residue which had two spots by TLC (chloroform-silica gel). Trituration of the residue with ether gave 0.4 g of 3-(4-chloro-2-pyrimidinyl)-benzaldehyde, mp 136°–138° C. (the slower moving spot) which was identified by analysis, PMR and IR.

The ether soluble material was concentrated in vacuo and refluxed with 30 ml of phosphorous oxychloride overnight and then treated as above, giving 3 g of crystals, mp 46°–48° C., which was identified by analysis, PMR and IR as 4-chloro-2-(3-dichloromethylphenyl)-pyrimidine.

EXAMPLE 39

3-(4-Chloro-2-pyrimidinyl)benzenemethanol

A 1.0 g portion of 3-(4-chloro-2-pyrimidinyl)benzaldehyde was dissolved in 230 ml of 2-propanol and 0.32 g of freshly ground sodium borohydride pellets was added. After stirring for 3 hours at 50°–60° C. in a water bath, the excess reducing agent was destroyed with 6N hydrochloric acid. The solution was neutralized with sodium bicarbonate and the mixture concentrated in vacuo. The residue was partitioned between ethyl acetate and water. The organic layer was dried over sodium sulfate and then evaporated, giving 1.1 g of the desired intermediate as a colorless oil.

EXAMPLE 40

4-Hydrazino-2-(3-tolyl)-pyrimidine

A 15.6 g portion of 4-chloro-2-(3-tolyl)pryimidine in 400 ml of methanol was heated to boiling. A 190 ml portion of hydrazine hydrate was then added and the solution was heated and stirred for 2 hours, then allowed to cool overnight. The mixture was diluted with 200 ml of water and cooled in an ice bath. The resulting solid was collected and recrystallized from 150 ml of ethanol, giving 3.9 g of the desired intermediate, mp 102°–103° C.

Following the procedure of Example 40 and using the indicated precursors, the intermediates of Examples 41–56, found in Table V, were obtained.

TABLE V

| Example | Precursor | Intermediate | MP °C. |
|---|---|---|---|
| 41 | Example 25 | 4-hydrazino-5-methyl-2-(3-nitrophenyl)-pyrimidine | 204–206 |
| 42 | Example 26 | 4-hydrazino-2-(3,5-ditrifluoromethylphenyl)-pyrimidine | 111–112 |
| 43 | Example 27 | 4-hydrazino-2-(N,N—dimethylamidophenyl)-pyrimidine | 165–167.5 |
| 44 | Example 28 | 4-hydrazino-2-(3-ethoxycarbonylphenyl)-pyrimidine | 170–173 |
| 45 | Example 29 | 4-hydrazino-2-(4-ethoxycarbonylphenyl)-pyrimidine | 161–163 |
| 46 | Example 38 | 4-hydrazino-2-(3-dichloromethylphenyl)-pyrimidine | |
| 47 | Example 30 | 4-hydrazino-2-(3-bromophenyl)-pyrimidine | 136–138 |
| 48 | Example 31 | 4-hydrazino-2-(3-difluoromethoxyphenyl)-pyrimidine | 73–76.5 |
| 49 | Example 32 | 4-hydrazino-2-(3-methyl-4-pyridinyl)-pyrimidine | |
| 50 | Example 33 | 4-hydrazino-5-methyl-2-[3-trifluoromethyl)phenyl]-pyrimidine | 193–195 |
| 51 | Example 39 | 3-(4-hydrazino-2-pyrimidinyl)-benzenemethanol | 154–158 |
| 52 | Example 34 | 4-hydrazino-2-(3-nitrophenyl)-pyrimidine | 208–209 |
| 53 | Example 35 | 4-hydrazino-2-(2-pyridinyl)-pyrimidine | 108–110 |
| 54 | Example 36 | 4-hydrazino-2-(3-pyridinyl)-pyrimidine | 107–108 |
| 55 | 4-chloro-2-(4-pyridinyl)-pyrimidine | 4-hydrazino-2-(4-pyridinyl)-pyrimidine | 208–212 |
| 56 | Example 37 | 4-hydrazino-6-methyl-2-[3-trifluoromethyl)phenyl]-pyrimidine | 141–143.5 |

EXAMPLE 57

5-(3-Methylphenyl)[1,2,4]triazolo[1,5-c]pyrimidin-2-amine

A 2.74 g portion of 4-hydrazino-2-(3-tolyl)pyrimidine was dissolved in 100 ml of methanol. Next, a 1.5 g portion of cyanogen bromide was added and the mixture was refluxed for 3 hours, then allowed to cool overnight. After evaporating the reaction, the residue was stirred in a mixture of 25 ml of chloroform and saturated aqueous potassium bicarbonate. The chloroform layer was separated, dried and evaporated, giving an oil which solidified and was then recrystallized from methylene chloride-hexane, giving 550 mg of the desired product as a tan solid, mp 125°–126° C.

Following the general procedure of Example 57 and using the indicated intermediates, the products of Examples 58–75, found in Table VI, were obtained.

TABLE VI

| Example | Intermediate | Product | MP °C. |
|---|---|---|---|
| 58 | Example 41 | 8-methyl-5-(3-nitrophenyl)-[1,2,4]triazolo[1,5-c]pyrimidin-2-amine | 240–242 |
| 59 | Example 42 | 5-[3,5-bis(trifluoromethyl)phenyl][1,2,4]triazolo[1,5-c]-pyrimidin-2-amine | 164–167 |
| 60 | Example 43 | 3-(2-amino[1,2,4]triazolo-[1,5-c]pyrimidin-5-yl)-N,N—dimethylbenzamide | 213.5–215.5 |
| 61 | Example 44 | 3-(2-amino[1,2,4]triazolo-[1,5-c]pyrimidin-5-yl)benzoic acid, ethyl ester | 124.5–127 |

TABLE VI-continued

| Example | Intermediate | Product | MP °C. |
|---|---|---|---|
| 62 | Example 45 | 4-(2-amino[1,2,4]triazolo-[1,5-c]pyrimidin-5-yl)benzoic acid, ethyl ester | 180.5–181.5 |
| 63 | Example 46 | 5-[3-(dichloromethyl)phenyl]-[1,2,4]triazolo[1,5-c]pyrimidin-2-amine | 146–148 |
| 64 | Example 47 | 5-(3-bromophenyl)[1,2,4]-triazolo[1,5-c]pyrimidin-2-amine | 175–177 |
| 65 | Example 48 | 5-[3-(difluoromethoxy)phenyl]-[1,2,4]triazolo[1,5-c]pyrimidin-2-amine | 115–117 |
| 66 | Example 49 | 5-(3-methyl-4-pyridinyl)-[1,2,4]triazolo[1,5-c]pyrimidin-2-amine | 133–134 |
| 67 | 4-hydrazino-2-[3-(trifluoromethyl)phenyl]-pyrimidine | 5-[3-(trifluoromethyl)phenyl]-[1,2,4]triazolo[1,5-c]pyrimidin-2-amine | 119–122 |
| 68 | 4-hydrazino-2-(4-fluorophenyl)pyrimidine | 5-(4-fluorophenyl)[1,2,4]-triazolo[1,5-c]pyrimidin-2-amine | 215 |
| 69 | 4-hydrazino-2-(3-chlorophenyl)pyrimidine | 5-(3-chlorophenyl)[1,2,4]-triazolo[1,5-c]pyrimidin-2-amine | 192–194 |
| 70 | Example 52 | 5-(3-nitrophenyl)[1,2,4]-triazolo[1,5-c]pyrimidin-2-amine | 272–276 |
| 71 | Example 50 | 8-methyl-5-[3-(trifluoromethyl)phenyl[1,2,4]triazolo-[1,5-c]pyrimidin-2-amine | 179–181 |
| 72 | Example 54 | 5-(3-pyridinyl)[1,2,4]triazolo[1,5-c]pyrimidin-2-amine | 228–231 |
| 73 | Example 53 | 5-(2-pyridinyl)[1,2,4]triazolo[1,5-c]pyrimidin-2-amine | 187–189 |
| 74 | Example 55 | 5-(4-pyridinyl)[1,2,4]triazolo[1,5-c]pyrimidin-2-amine | >250 |
| 75 | Example 56 | 7-methyl-5-[3-(trifluoromethyl)phenyl][1,2,4]triazolo-[1,5-c]pyrimidin-2-amine | 186.5–189 |

EXAMPLE 76

5-[3-(Trifluoromethyl)phenyl][1,2,4]triazolo[1,5-c]pyrimidin-2-acetamide

A mixture of 1.0 g of 5-[3-(trifluoromethyl)phenyl][1,2,4]triazolo[1,5-c]pyrimidin-2-amine, 25 ml of acetic anhydride and 50 ml of anhydrous ether was heated on a steam bath for 5 hours and then cooled. The solid was collected, washed with water, dried and recrystallized from chloroform, giving 1.02 g of solid. This solid was dissolved in warm ethyl acetate, washed with saturated aqueous sodium bicarbonate, then water, dried and the solvent removed in vacuo. The residue was recrystallized from petroleum ether, giving 780 mg of the desired product, mp 218°–220° C.

EXAMPLE 77

N-[8-Methyl-5-(3-nitrophenyl)[1,2,4]triazolo[1,5-c]pyrimidin-2-yl]acetamide

A 12.7 g portion of 8-methyl-5-(3-nitrophenyl)[1,2,4]-triazolo[1,5-c]pyrimidin-2amine and 306 mg of 4-dimethylaminopyridine in 150 ml of pyridine:acetic anhydride (2:1) was refluxed with stirring for one hour. The solution was cooled and then evaporated to dryness. The residue was slurried in 100 ml of ether and the brown crystals collected. These were dissolved in 1200 ml of hot ethanol, filtered and the filtrate concentrated to 200 ml and cooled. The crystals were collected, giving 11.3 g of the desired product, mp 245°–247° C.

EXAMPLE 78

N-[8-Methyl-5-[3-[[(4-methylphenyl)sulfonyl]amino]-phenyl][1,2,4]triazolo[1,5-c]pyrimidin-2-yl]acetamide A 5.0 g portion of N-[8-methyl-5-(3-nitrophenyl)[1,2,4]triazolo[1,5-c]pyrimidin-2-yl]acetamide in a solution of 20 ml of trifluoroacetic acid containing 500 mg of 10% palladium on carbon catalyst was shaken under 46 lb. of hydrogen pressure on a Paar hydrogenator overnight. The mixture was filtered and the filtrate evaporated, giving an oil. This oil was neutralized with 20 ml of saturated aqueous potassium carbonate, saturated with salt and extracted into 100 ml of ethyl acetate. The organic phase was dried, filtered and evaporated. The residue was recrystallized from ethanol, giving 3.4 g of N-[5-(3-aminophenyl)-8-methyl[1,2,4]-triazolo[1,5-c]pyrimidin-2-yl]acetamide. A 282 mg portion of the above compound and 210 mg of p-toluene sulfonyl chloride were dissolved in 100 ml of pyridine with stirring and sealed overnight. A 105 mg portion of p-toluene sulfonyl chloride was added and the mixture was warmed under a drying tube on a steam bath for ½ hour. The mixture was cooled, evaporated and the residue taken up in chloroform and passed through a hydrous magnesium silicate pad. The filtrate was taken up in chloroform, washed with 0.1N hydrochloric acid, dried and evaporated. This residue was recrystallized from ethyl acetate-cyclohexane, giving the desired product as white crystals, mp 215°–218° C.

EXAMPLE 79

N-Methyl-5-[3-trifluoromethyl)phenyl][1,2,4]-triazolo[1,5-c]pyrimidin-2-amine

A mixture of 8.0 g of 5-[3-(trifluoromethyl)-phenyl][1,2,4]triazolo[1,5-c]pyrimidin-2-acetamide, 75 ml of dry N,N-dimethylformamide and 1.31 g of 50% sodium hydride in oil was stirred for 1.5 hours until foaming stopped and a solution formed. A 3.10 ml (7.07 g) portion of iodomethane was added and after ½ hour the mixture was heated on a steam bath for 30 minutes followed by concentration in vacuo. The residue was distributed between water at pH 8 containing potassium bicarbonate and chloroform. The organic layer was dried and evaporated and the residue recrystallized from carbon tetrachloride, giving 4.62 g of 2-(N-acetyl-N-methyl)amino-5-[3-(trifluoromethyl)phenyl][1,2,4]-triazolo[1,5-c]pyrimidine.

A 3.35 g portion of the above pyrimidine was dissolved in 100 ml of tetrahydrofuran and 50 ml of ethanol. To this was added 4.15 ml of 6N hydrochloric acid and 4.15 ml of water. The mixture was allowed to stand one week, aqueous potassium bicarbonate was added and the mixture was allowed to evaporate. The residue was crystallized from 40 ml of ethyl acetate giving 1.80 g of the desired product as light yellow crystals, mp 177.5°–179° C.

EXAMPLE 80

3-(2-Amino[1,2,4]triazolo[1,5-c]pyrimidin-5-yl)benzaldehyde 3-(4-Hydrazino-2-pyrimidinyl)benzenemethanol was converted to 3-(2-amino[1,2,4]triazolo[1,5-c]pyrimidin-5-yl)benzenemethanol by the procedure of Example 57.

A 100 mg portion of the above triazolo derivative and 700 mg of freshly prepared dimethylaminopyridinium chlorochromate in 100 ml of chloroform was stirred overnight. A 700 mg portion of the chromate reagent was added and the mixture was stirred for 24 hours. The mixture was filtered and the filter cake eluted several times with 2% methanol in chloroform. The solvents were evaporated giving 50 mg of the desired product as a grey solid, mp 205°–208° C.

EXAMPLE 81

5-(4-Pyridinyl)[1,2,4]triazolo[1,5-c]pyrimidin-2-amine, pyridine-1-oxide

A 212 mg portion of 5-(4-pyridinyl)[1,2,4]-triazolo[1,5-c]pyrimidin-2-amine was dissolved in 400 ml of dichloromethane. A 236 mg portion of m-chloroperbenzoic acid was added, the mixture was stirred 24 hours and the insolubles removed by filtration. The filtrate was concentrated to 20 ml and the resulting crude solid collected. This solid was crystallized from 40 ml of absolute ethanol, giving 70 mg of the desired product, mp 274°–277° C. (dec.).

EXAMPLE 82

1-Chloro-3-[[5-[3-(trifluoromethyl)phenyl][1,2,4]-triazolo[1,5-c]pyrimidin-2-yl]amino]-2-propanol A mixture of 7.68 g of 5-[3-(trifluoromethyl)-phenyl][1,2,4]triazolo[1,5-c]pyrimidin-2-acetamide, 75 ml of N,N-dimethylformamide and 1.26 g of 50% sodium hydride in oil was stirred for 1.5 hours. A 2.24 ml (2.65 g) portion of epichlorohydrin was added and the mixture was heated on a steam bath for one hour and then concentrated in vacuo to a residue. The residue was taken up in dilute hydrochloric acid, then raised to pH 8 with potassium bicarbonate and extracted three times with chloroform. The organic layers were combined, dried and evaporated. The residue was taken up in 25 ml of methanol, cooled and filtered. The filtrate was concentrated in vacuo and the residue taken up in chloroform and passed through hydrous magnesium silicate. The filtrate was concentrated in vacuo and the residue taken up in 20 ml of ethyl acetate and cooled. This solution was column chromatographed on silica gel. Fractions 5 and 6 were combined and recrystallized from 10 ml of methanol, giving 1.43 g of off-white crystals.

These crystals were dissolved in 10 ml of tetrahydrofuran and treated with 2 ml of 6N hydrochloric acid. After 3 hours the reaction was stopped by adding aqueous potassium bicarbonate and stripping the tetrahydrofuran. The residue was dissolved in 150 ml of chloroform with warming. The organic layer was separated, dried, concentrated in vacuo and recrystallized from methanol, giving 0.45 g of the desired product as white crystals, mp 141°–142° C.

EXAMPLE 83

N-[5-[3-[[(4-Methylphenyl)sulfonyl]amino]phenyl]-[1,2,4]triazolo[1,5-c]pyrimidin-2-yl]acetamide N-[5-(3-nitrophenyl)[1,2,4]triazolo[1,5-c]pyrimidin-2-yl]acetamide was converted to N-[5-(3-amino phenyl)[1,2,4]triazolo]1,5-c]pyrimidin-2-yl]acetamide by the procedure of Example 78.

A 3.9 g portion of the above compound was reacted with p-toluene sulfonyl chloride as described in Example 78, giving 1.95 g of the desired product as beige crystals, mp 208°–211° C.

EXAMPLE 84

N-[3-(2-Amino[1,2,4]triazolo[1,5-c]pyrimidin-5yl) phenyl]-4-methylbenzenesulfonamide A 250 mg portion of N-[5-[3-[[(4-methylphenyl) sulfonyl]amino]phenyl][1,2,4]triazolo[1,5-c]pyrimidin-2-yl]acetamide was dissolved in 30 ml of dioxane. A 15 ml portion of 1N hydrochloric acid was added, the mixture was allowed to stand 22 hours, concentrated, neutralized with aqueous potassium bicarbonate and extracted with ethyl acetate. The organic extract was evaporated and the residue taken up in 1% methanol in chloroform and filtered through hydrous magnesium silicate. The filtrate was evaporated and the residue crystallized from ethyl acetatecyclohexane giving 15 mg of the desired product as white crystals, mp 205°–208° C.

EXAMPLE 85

5-(3-Ethynylphenyl)[1,2,4]triazolo[1,5-c]pyrimidin-2-amine

A suspension of 2.0 g of 5-(3-bromophenyl) [1,2,4]triazolo[1,5-c]pyrimidin-2-amine in 45 ml of triethylamine was flushed with argon and stirred 15 minutes. A 17 mg portion of palladium II acetate and 34 mg of triphenyl phosphine were added followed by 1.06 g of ethynyl trimethylsilane. The mixture was heated to reflux, then allowed to stand overnight under argon, then again heated at reflux for 5 hours and then cooled. A 34 mg portion of palladium II acetate, 68 mg of triphenyl phosphine and 2.12 g of ethynyl trimethylsilane were added and this mixture was refluxed 15 hours. The mixture was cooled, evaporated, taken up in 200 ml of chloroform, washed with 100 ml of saturated aqueous potassium bicarbonate, dried, filtered and evaporated giving a brown glass. This glass was taken up in 50 ml of methanol and 200 mg. of anhydrous potassium carbonate were added. This mixture was sealed, stirred overnignt and then evaporated. The residue was taken up in 100 ml of chloroform, washed with 50 ml of dilute aqueous potassium bicarbonate, dried, filtered through hydrous magnesium silicate and evaporated. This solid was crystallized from chloroform-cyclohexane, giving 300 mg of the desired product, mp 170°–172° C.

EXAMPLE 86

5-(3-Iodophenyl)[1,2,4]triazolo[1,5c]pyrimidin-2-amine

A mixture of 148 g of m-iodobenzoic acid, 46.2 ml of thionyl chloride and 1300 ml of toluene was heated under a drying tube. After ½ hour the starting material dissolved. The mixture was then heated at reflux for ½ hour then allowed to cool and the solvent removed in vacuo. The resulting yellow liquid was immediately dissolved in 800 ml of tetramethylene sulfone and 69.2 g of sulfamide were added. This mixture was stirred and heated for 15 minutes at 130° C., an exotherm raised the temperature to 160° C. then the mixture was heated at 130° C. for 2 hours and then allowed to cool for 48 hours. The mixture was then partitioned between 800 ml. of ether and one liter of water. The ether layer was filtered, the filtrate washed four times with water, then dried, filtered and evaporated. The resulting brown liquid was distilled in a Kugelrohr (90°–95° C.) to give 112 g of 3-iodobenzonitrile as a colorless liquid which crystallized on standing.

A mixture of 110.6 g of 3-iodobenzonitrile, 29.4 ml of methanol and 1300 ml of ether was cooled to 5° C. in an ice bath and hydrogen chloride gas was passed into the solution, with rapid stirring, for 3.5 hours. The mixture was then refrigerated overnight and the resulting crystals collected, washed with ether and dried. These crystals were dissolved in 1300 ml of ethanol, cooled to 5° C. in an ice bath and ammonia gas was passed through the solution for 1.5 hours. The mixture was refrigerated for 3 days, then filtered and the ethanol evaporated at 45° C. leaving a gum. This gum was triturated twice with 100 ml of ether giving 128 g of 3-iodobenzamidine hydrochloride. This 128 g was then reacted with ethyl propionate in ethanolic potassium hydroxide with heat for 2 hours, then allowed to cool overnight with stirring. The solvent was then evaporated at 50° C., giving a gum. This gum was triturated with 800 ml of water and 200 ml of ether. The aqueous phase was separated, acidified to pH 5 with 6N hydrochloric acid and the resulting solid collected giving 2-(3-iodophenyl)-4-(1H)-pyrimidinone.

A 32.9 g portion of 2-(3-iodophenyl)-4((1H)-pyrimidinone was stirred and refluxed in 123 ml. of phosphorus oxychloride for 2 hours, then cooled overnight and the solvent evaporated at 55° C. The residue was suspended in 400 ml of chloroform, then evaporated. This residue was taken up in 300 ml of chloroform, filtered and washed twice with 75 ml of chloroform. The combined filtrate and washes were evaporated giving 4-chloro-2-(3-iodophenyl)pyrimidine.

A mixture of 20.7 g of 4-chloro-2-(3-iodophenyl)-pyrimidine, 140 ml of water and 80 ml of hydrazine hydrate was heated on a steam bath to produce solution, then refluxed ½ hour and allowed to cool overnight. The resulting crystals were collected, washed with methanol:water (1:1) and dried, giving 4-hydrazino-2-(3-iodophenyl)pyrimidine.

A 15.6 g portion of 4-hydrazino-2-(3-iodophenyl)-pryimidine was stirred in 260 ml of methanol and 7.95 g of cyanogen bromide was added. This mixture was refluxed for 2 hours, cooled overnight and then 75 ml of saturated aqueous potassium carbonate added. The methanol was evaporated and the residue partiitoned between water and chloroform. The chloroform layer was washed twice with water, dried, filtered and the filtrate evaporated giving, after recrystallization from ethanol, 6.55 g of the desired product as white crystals, mp 179°-181° C.

EXAMPLE 87

5-(3-Bromo-4-fluorophenyl)[1,2,4]triazolo[1,5-c-]pyrimidin-2-amine.

Using the method of Example 86, 3-bromo-4-fluorobenzonitrile is converted to 5-(3-bromo-4-fluorophenyl [1,5-c]pyrimidin-2-amine.

EXAMPLE 88

5-(2-Fluorophenyl)[1,2,4]triazolo[1,5-c]pyrimidin-2-amine

Using the method of Example 86, 2-fluorobenzonitrile is converted to the title compound.

We claim:

1. Compounds of the structural formula:

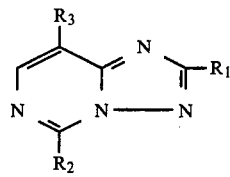

wherein $R_1$ is amino, acyl($C_1$-$C_4$)amino or alkyl($C_1$-$C_4$)amino; $R_2$ is selected from the group consisting of 2-pyridyl, 3-pyridyl, 4-pyridyl, 2-pyridine-1-oxide, 3-pyridine-1-oxide, 4-pyridine-1-oxide, 3-alkyl($C_1$-$C_4$)-4-pyridyl and a moiety of the formula:

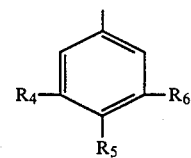

wherein $R_4$, $R_5$ and $R_6$ are each individually selected from the group consisting of hydrogen, chloro, bromo, iodo, nitro, trifluoromethyl, formyl, ethynyl, alkyl($C_1$-$C_4$), difluoromethoxy, carboxamido, dialkyl($C_1$-$C_4$)carbamyl, -CON(CH$_2$)$_4$, -CON(CH$_2$)$_5$, -CO$_2$ alkyl($C_1$-$C_4$) and p-tolylsulfonylamino; and $R_3$ is hydrogen or alkyl($C_1$-$C_4$) with the first proviso that $R_4$, $R_5$ and $R_6$ may not simultaneously be hydrogen and with the second proviso that $R_2$ may not be p-trifluoromethylphenyl, 4-chlorophenyl or 3,5-dichlorophenyl.

2. Compounds of the structural formula:

wherein $R_1$ is amino, acyl($C_1$-$C_4$)amino or alkyl($C_1$-$C_4$)amino; $R_2$ is 2-pyridyl, 3-pyridyl, 4-pyridyl, 2-pyridine-1-oxide, 3-pyridine-1-oxide, 4-pyridine-1-oxide or 3-alkyl($C_1$-$C_4$)-4-pyridyl; and $R_3$ is hydrogen or alkyl($C_1$-$C_4$).

3. The compound according to claim 1; 5-(3,5-bis(trifluoromethyl)phenyl)[1,2,4]triazolo[1,5-c]pryimidin -2-amine.

4. The compound according to claim 1; 4-(2-amino [1,2,4]triazolo[1,5-c]pyrimidin-5-yl)benzoic acid, ethyl ester.

5. The compound according to claim 1; 5-(3-bromophenyl)[1,2,4]triazolo[1,5, c]pyrimidin-2-amine.

6. The compound according to claim 1; 5-(3- -(difluoromethoxy)phenyl)[1,2,4]triazolo[1,5-c]pyrimidin-2-amine.

7. The compound according to claim 1; 5-(3-methyl-4-pyridinyl)[1,2,4]triazolo[1,5-c]pyrimidin-2-amine.

8. The compound according to claim 1; 5-(3-trifluoromethyl)phenyl)[1,2,4]triazolo[1,5-c]pyrimidin-2-amine.

9. The compound according to claim 1; 5-(3-chlorophenyl)[1,2,4]triazolo[1,5-c]pyrimidin-2-amine.

10. The compound according to claim 1; 5-(3-nitrophenyl)[1,2,4]triazolo[1,5-c]pyrimidin-2-amine.

11. The compound according to claim 1; N-methyl-5-(3-(trifluoromethyl)phenyl)[1,2,4]triazolo[1,5-c]pyrimidin-2-amine.

12. The compound according to claim 1; 3-(2-amino[1,2,4]triazolo[1,5-c]pyrimidin-5-yl)benzaldehyde.

13. The compound according to claim 1; 5-(4-pyridinyl-1-oxide)[1,2,4]triazolo[1,5-c]pyrimidin-2-amine.

14. The compound according to claim 1; N-(5-(3-(4-methylphenyl)sulfonylamino)phenyl)[1,2,4]triazolo[1,5-c]pyrimidin-2-yl]acetamide.

15. The compound according to claim 1; N-(3-(2-amino[1,2,4]triazolo[1,5-c]pyrimidin-5-yl)phenyl)-4-methylbenzenesulfonamide.

16. The compound according to claim 1; 3-(2-amino[1,2,4]triazolo[1,5-c]pyrimidin-5-yl)-N,N-dimethylbenzamide.

17. A method of treating asthma and allergic disease in a mammal which comprises administering to said mammal an effective amount of a compound of claim 1.

18. An anti-asthmatic composition of matter in dosage unit form comprising from about 7 mg. to about 1.8 gm. of a compound of claim 1.

19. The compound according to claim 1; 5-(3-pyridinyl)[1,2,4]triazolo[1,5-c]pyrimidin-2-amine.

20. The compound according to claim 1; 5-(4-pyridinyl)[1,2,4]triazolo[1,5-c]pyrimidin-2amine.

* * * * *